United States Patent [19]

Westwood et al.

[11] Patent Number: 5,478,323

[45] Date of Patent: Dec. 26, 1995

[54] MANIFOLD FOR INJECTION APPARATUS

[75] Inventors: Donald C. Westwood, Cupertino; Stephen J. Schoenberg, Redwood City; Don S. Minami, Monte Sereno, all of Calif.

[73] Assignee: Eli Lilly and Company, Indianapolis, Ind.

[21] Appl. No.: 333,207

[22] Filed: Nov. 2, 1994

Related U.S. Application Data

[63] Continuation-in-part of Ser. No. 41,758, Apr. 2, 1993, abandoned.

[51] Int. Cl.⁶ .................................................. A61M 3/00
[52] U.S. Cl. .............................. 604/191; 604/83; 604/90; 604/232; 604/237
[58] Field of Search .................... 604/191, 90, 82–83, 604/211, 232, 237, 205, 186, 135, 240

[56] References Cited

U.S. PATENT DOCUMENTS

| | | |
|---|---|---|
| 3,767,085 | 10/1973 | Cannon . |
| 4,359,049 | 11/1982 | Redl . |
| 4,610,666 | 9/1986 | Pizzino . |
| 4,689,042 | 8/1987 | Sarnoff . |
| 4,755,169 | 7/1988 | Sarnoff . |
| 4,795,433 | 1/1989 | Sarnoff . |
| 4,978,336 | 12/1990 | Capozzi . |
| 4,979,942 | 12/1990 | Wolf . |
| 5,116,315 | 5/1992 | Capozzi . |
| 5,147,323 | 9/1992 | Haber . |
| 5,199,949 | 4/1993 | Haber . |
| 5,240,146 | 8/1993 | Smedley . |
| 5,253,785 | 10/1993 | Haber . |
| 5,271,527 | 12/1993 | Haber . |
| 5,286,258 | 2/1994 | Haber . |
| 5,298,023 | 3/1994 | Haber . |
| 5,314,412 | 5/1994 | Rex . |
| 5,329,976 | 7/1994 | Haber . |

FOREIGN PATENT DOCUMENTS

| | | |
|---|---|---|
| WO93/25251 | 12/1993 | WIPO . |
| WO94/11039 | 5/1994 | WIPO . |

*Primary Examiner*—C. Fred Rosenbaum
*Assistant Examiner*—P. VanOver
*Attorney, Agent, or Firm*—Baker & Daniels

[57] ABSTRACT

A removable manifold assembly for attachment to the outlet end of a multi-cartridge injection device. The manifold assembly comprises two rigid plastic housings which encapsulate a rubber septum. Check valves are formed by compressing the front surface of the septum against a seal face of the rear housing to form a fluid tight interface therebetween. A first fluid path is formed from each cartridge in the injector through the manifold assembly to a patient delivery needle. A second fluid path is formed in the manifold assembly from the first fluid path to a back surface of the septum in order to enable a residual fluid force to be exerted against the back surface of the septum, thereby forcing the respective check valve in its closed position. The manifold assembly includes a unique geometry that permits the manifold to be snapped into engagement with the housing only when properly oriented with the housing. In one embodiment, the manifold assembly is designed to slip over the proximal ends of the cartridge retainers prior to snapping into engagement with the injector housing. In this embodiment, the manifold and cartridge containers are configured so that the manifold is able to slip over the cartridge retainers only when the cartridge retainers have been rotated into their locked positions within the injector housing.

5 Claims, 6 Drawing Sheets

MANIFOLD FOR INJECTION APPARATUS

CROSS-REFERENCE TO RELATED APPLICATION

This is a continuation-in-part of the U.S. patent application Ser. No. 08/041,758, filed Apr. 2, 1993 now abandoned entitled "MANIFOLD MEDICATION INJECTION APPARATUS AND METHOD".

BACKGROUND OF THE INVENTION

The present invention relates generally to devices for injecting two or more medications simultaneously and, more particularly, to a removable manifold assembly that is attachable to the outlet end of the injection device for mixing the two medications and discharging the mixed medications through a single needle.

It is medically desirable in the treatment of certain conditions of the human body to administer two or more types of medications simultaneously. The treatment of diabetes is one such example. Under certain conditions, it is desirable to simultaneously deliver two types of insulin, fast-acting insulin and an intermediate-acting insulin, such as isophane insulin, which takes effect more slowly but for a longer period of time. Also, a longer-acting type of insulin called ultralente is available. In order to most accurately simulate the natural glucose curve of the body, the insulin user would need to inject different ratios or combinations of these insulins several times daily.

In order to achieve such injection capability, there have been developed injection devices in which separate cartridges of a desired medication are housed. It is desirable that both medications be delivered to a patient through a single needle instead of two or more needles. Therefore, such injection devices must have a manifold assembly that enables the medications to be mixed together prior to injection.

An example of such an injection device is disclosed in U.S. Pat. No. 5,253,785. This patent discloses a manifold assembly consisting of a rear piece (spike adaptor 116) and a front piece (manifold 118), both made of hard plastic, and rubber check valve body disposed therebetween. The check valve body includes a pair of cup-shaped members, each having an internal conical surface positioned to engage an external conical surface formed by the outside of a respective hollow projection in the front piece to form a check valve. Normally, the check valves are closed thereby preventing fluid flow from a common pathway that fluidly connects to the interior of the needle cannula. Upon pressurization of the interior of one of the cartridges, the corresponding check valve is opened by deformation of the check valve body. To permit this deformation, there is an annular gap surrounding the cup-shaped members and a further gap in the space between that portion of the check valve body adjacent to the cup-shaped members and the rear piece.

Another type of manifold assembly is disclosed in U.S. Pat. No. 5,271,527. This manifold assembly is removable from the cartridge housing of the dispenser in order to permit the removal and replacement of the spent cartridges of medication. A pair of manifold assembly release buttons are mounted to the housing. To remove the manifold from the housing, the release buttons are forced toward the manifold assembly until pegs extending from the cartridge housing become disengaged from holes formed in tabs on the manifold housing, thereby permitting the user to pull the manifold assembly away from the housing.

Another type of manifold assembly is disclosed in PCT International Application Number PCT/US93/11044 (International Publication Number WO 94/11039). This application discloses a dual chamber pharmaceutical dispenser having a manifold including a check valve associated with each chamber for permitting fluid flow from the chamber into the manifold flow path. These check valves are each formed by a valve insert and a cylindrical elastic band mounted over the valve insert to permit the flow of liquid pharmaceutical in one direction only. A ball check valve is provided to prevent the flow of fluid from the pharmaceutical chamber to the needle assembly. Upon depressing the manifold shield to initiate an injection, the ball of the check valve is moved away from the valve seat to permit fluid flow through the needle cannula.

Although the disclosed manifold check valves are designed to prevent the flow of fluid back into the pharmaceutical reservoirs, these valves may experience wear and deformation over time, resulting in leakage. It is desired to provide a manifold assembly that improves upon known check valve structures in order to more positively prevent a reverse flow of fluid back into the pharmaceutical reservoirs. In addition, it is desired to provide a removable manifold assembly for a reusable injection dispenser that minimizes the likelihood of contamination of the cartridges upon placement of the manifold onto the new cartridges.

SUMMARY OF THE INVENTION

The present invention provides a removable manifold assembly for attachment to the outlet end of a multi-cartridge injector, wherein a series of channels are formed within the manifold housing which enable a positive fluid pressure or force to be exerted onto the back surface of a check valve in the manifold assembly in order to positively close the valve, thereby reducing the likelihood of inadvertent fluid flow into or out of the check valve. In addition, the present invention provides a manifold assembly having a unique geometry that enables the manifold to be attached to the injector only when the cannulas in the manifold are properly aligned with their respective cartridges.

Generally, the present invention provides a removable manifold assembly for attachment to the outlet end of a multi-cartridge injection device, wherein the manifold includes a first cannula in fluid communication with a first cartridge and a second cannula in communication with a second cartridge. The manifold includes a first fluid path extending from the first cannula to a patient delivery needle secured to the manifold, and a second fluid path extending from the second cannula to the patient delivery needle. The manifold includes a pressure-activated one-way check valve in at least one of the fluid paths (e.g., the second fluid path), wherein a pressure exerted on a front surface of the check valve opens the check valve to allow fluid flow therethrough. The manifold includes a third fluid path extending from the first fluid path to the back surface of the check valve. Upon the flow of pressurized fluid in the first fluid path, a portion of the fluid will flow through the third fluid path and exert a fluid pressure on the back surface of the check valve.

More specifically, the invention provides, in one form thereof, a manifold assembly comprising two rigid plastic housings which encapsulate a rubber septum. Two metal cannulas are affixed to the respective inlet ports of the rear housing to provide inlets of the respective medications from their cartridges. The exit channel is formed by a standard needle inserted into the cylindrical portion of the septum through an opening in the front housing. The surface of the rear housing in engagement with a front surface of the septum comprises a seal face. The check valves are formed by compressing or "preloading" the front surface of the septum against the seal face to form a fluid-tight interface therebetween. Each check valve is positioned over its respective inlet port.

Upon delivery of one of the medications, the medication enters the cannula under pressure, which causes the pressure at the inlet port to exceed the pressure in the manifold fluid path. This pressure causes a temporary deformation of the front face of the septum, resulting in an opening of the check valve to allow fluid to flow therethrough and into a first recessed portion of the rear housing that is in communication with the delivery needle. After delivery is complete, the fluid pressure at the inlet port decreases sufficiently to close the check valve, i.e. the front face septum returns to its initial "nondeformed" position in fluid-tight engagement with the seal face of the rear housing.

The septum includes an opening adjacent the check valve. This opening is in communication with the first recessed portion in the rear housing. Some of the residual fluid remaining in the first recessed portion after injection will migrate into the opening in the septum and into a second recessed portion in the front housing behind the portion of the septum comprising the check valve. Fluid in this second recessed portion exerts a pressure on the back surface of the septum thereby causing further compression between the front surface of the septum and the seal face to ensure a fluid tight seal therebetween.

The present invention provides, in another form thereof, a manifold assembly having a series of projections and recesses on the inner surface of the front manifold housing. The outlet or proximal end of the injector housing includes corresponding projections and recesses such that, upon fastening the manifold housing to the end of the injector housing, the respective projections and recesses mate with one another to form a tight, snap-fit engagement if the manifold is properly oriented with respect to the end of the housing. However, if the manifold is oriented improperly with respect to the housing, i.e., rotated 180 with respect to its proper orientation, the respective recesses and projections do not fit with one another, thereby preventing the manifold from being snap fit onto the housing and indicating to the user that the manifold is not properly oriented with respect to the housing.

In another embodiment of the present invention, plastic cartridge retainers are provided for housing the cartridges within the injector housing. When installed in the housing, the retainers extend beyond the outlet end of the housing, and the manifold assembly is inserted over the distal ends of the retainers and into a snap-fit engagement with the end of the injector housing. The proximal ends of the retainers each include a bayonet coupling which fits into a respective bayonet socket formed within the injector housing. To secure the retainers to the housing, the protrusions on the bayonet coupling for each retainer are inserted into the appropriate grooves of a respective bayonet socket in the housing. The retainer is then rotated to lock the retainer into the respective bayonet socket.

The distal ends of each of the cartridge retainers includes protrusions and grooves that correspond to the respective grooves and protrusions on the manifold assembly once the retainers are locked within the injector housing. If the retainers have been inserted into the bayonet sockets, but have not been rotated into their locked positions, the manifold assembly cannot be secured over the distal ends of the retainers, thereby indicating to the user that the cartridge retainers have not been rotated into their locked positions.

An advantage of the manifold assembly of the present invention is that it provides a hydraulic valve-closing force on each of the check valves in order to positively seal the check valves from fluid leaking back into the respective cannulas and into the cartridges.

Another advantage of the manifold assembly of the present invention is that the manifold housing has a unique geometry that permits the manifold assembly to be snapped into engagement with the injector housing only when the manifold assembly has been properly rotationally oriented with respect to the distal end of the injector housing, thereby ensuring that the manifold assembly is properly installed prior to use.

Other advantages of the present invention will be realized in the detailed description of the invention.

The present invention provides, in one form thereof, a medication dispensing device for effecting simultaneous delivery of two injectable products to a patient. The dispensing device includes a housing and first and second containers mounted to the housing. Each of the containers includes a plunger, an exit end, and an injectable product between the plunger and the exit end. Drive stems are disposed in the housing and are drivingly coupled to the respective plungers. A drive assembly is mounted to the housing and is drivingly coupled to the first and second drive stems to axially advance the first and second drive stems upon actuation of the drive assembly, thereby axially advancing the first and second plungers to effect delivery of the first and second dosages out of the first and second containers, respectively. A manifold is secured to the exit ends of the first and second cartridges and comprises a manifold housing including a first cannula extending into the first cartridge and a second cannula extending into the second cartridge. The manifold housing includes a delivery needle therein for delivery therethrough of the mixed injectable product. A first fluid path for the first injectable product is formed in the manifold housing from the first cannula to the delivery needle. A second fluid path for the second injectable product is formed in the manifold housing from the second cannula to the delivery needle. The manifold further includes a pressure actuated valve in the second fluid path. The valve is sufficiently flexible to move in a first direction to open and thereby permit the flow therethrough of the second injectable product upon the expulsion of the second injectable product out of the second cannula. The manifold further includes a third fluid path between the first fluid path and the valve. The third fluid path is configured to divert a portion of the fluid flowing in the first fluid path to the third fluid path and onto the valve to create a fluid force on the valve in a second and opposite direction from the first direction.

DETAILED DESCRIPTION OF THE INVENTION

Figure 1:
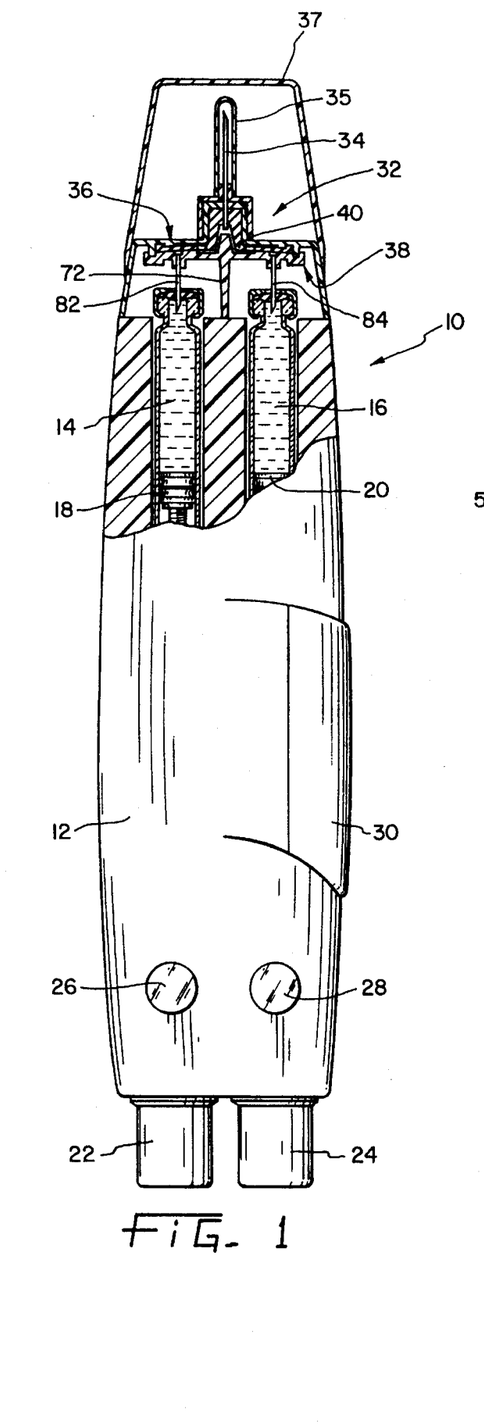
FIG. 1 is an elevational view of a first embodiment of wing-type dual medication injection apparatus, particularly showing in cross section, a manifold assembly in accordance with the present invention.

Referring to FIG. 1, there is shown an embodiment of a wing-type dual medication manifold injection apparatus 10 including an elongated main body 12, preferably made of a plastic material. At one end of body 12 there are supported two conventional glass cartridges or vials 14, 16 of different medications, such as for example, insulin, each having a respective plunger 18, 20 disposed therein. As an example, cartridge 14 may be a 3.0 milliliter diameter cartridge, and cartridge 16 may be a 1.5 milliliter diameter cartridge. One cartridge may contain regular insulin, and another cartridge may contain isophane or ultralente insulin, or any mixture thereof. Two metering knobs 22, 24 are provided for dialing in or setting the desired dosage to be dispensed from respective cartridges 14, 16 during injection. Dose indicators 26, 28 located adjacent respective metering knobs 22, 24, display the dosage amounts set.

In the embodiment shown in FIG. 1, a wing or lever mechanism 30 is shown for actuating the injection process. Details of a wing mechanism are disclosed in U.S. application Ser. No. 08/041,758, filed Apr. 2, 1993, the disclosure of which is incorporated herein by reference. It will be appreciated that the manifold assembly described in this application is applicable to a variety of medication injection devices. The disclosed wing-type injection device is merely one possible embodiment. The disclosed manifold assembly may also be used in conjunction with "plunger type" injection devices, such as illustrated in FIGS. 40 and 41 of U.S. application Ser. No. 08/041,758. In short, it will be recognized that the manifold assembly of the present invention may be used in conjunction with any type of injection apparatus containing two or more cartridges of medication to be injected.

A manifold assembly 32 in accordance with an embodiment of the present invention is disposed over the outlet end of injector 10 and onto cartridges 14, 16. Manifold assembly 32 functionally provides a fluid communication path between each cartridge 14, 16 and the patient needle 34. Needle 34 is covered by a protective needle cap 35, and the entire manifold assembly is covered by a cover 37.

Figure 2:
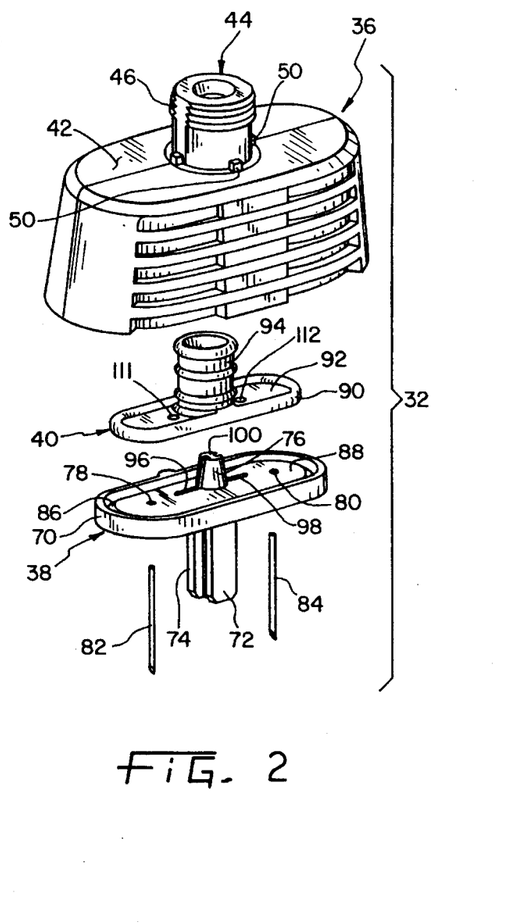
FIG. 2 is an enlarged, exploded perspective view of the manifold assembly of FIG. 1.

As illustrated in FIG. 2, the manifold assembly 32 comprises five components, a front housing 36, a rear housing 38, valve septum 40, and two cannulas 82, 84. The front and rear housings are preferably made of a rigid plastic material, such as ABS resin, and are preferably transparent in appearance. The septum is made of an elastomeric material, preferably butyl rubber.

Front housing 36 is shaped in the form of rectangular shroud having curved edges which taper or flare outwardly from top surface 42 toward the open bottom portion of the housing. A cylindrical collar 44 extends outwardly from surface 42. Collar 44 includes threads 46 that enable plastic needle assembly 48 (FIG. 3) to be threaded thereto. Collar 44 includes four small protuberances 50 spaced 90° apart from one another about the circumference of the base of the collar. Protuberances 50 serve as stops to limit the downward placement of needle assembly 46 on needle attachment portion 44.

Figure 6:
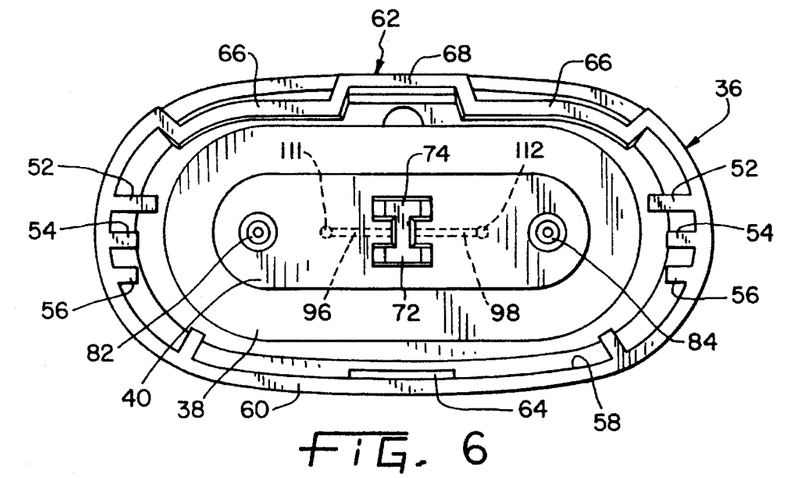
FIG. 6 is an enlarged plan end view of the manifold assembly of FIG. 1.

As shown in FIG. 6, the inner surface 58 of front housing 36 includes a number of small radially extending projections which are important to properly orient the manifold with respect to the distal end of injector apparatus 10. In particular, radially extending projections 52, 54, and 56 extend from each rounded end of inner surface 58. Projections 52 are the longest, and projections 56 are the shortest. The side surfaces 60 and 62 of inner surface 58 are quite distinct from one anther. Side surface 60 includes an elevated portion 64 which is generally centrally located along side surface 60 of inner surface 58. Side surface 62 includes a radially indented region 66 and a recessed region 68. The particular geometry of the inner surface 58 of front housing 36 is important in order to properly orient the housing with respect to injection apparatus 10, as shall be described infra.

Referring again to FIG. 2, rear housing 38 comprises an oval base portion 70, prongs 72 and 74 extending from the rear surface of the back housing, and a raised section 76. Rear housing 38 further includes two inlet ports 78, 80 (FIG. 3) which allow the insertion of steel cannulas 82, 84 respectively therein. Oval portion 70 includes a peripheral groove 86 and an inner seal face surface 88 (FIG. 4).

Rubber septum 40 includes a beaded peripheral edge 90, an expandable body portion 92, and a cylindrical center portion 94, which is pierced by needle 34.

Figure 3:
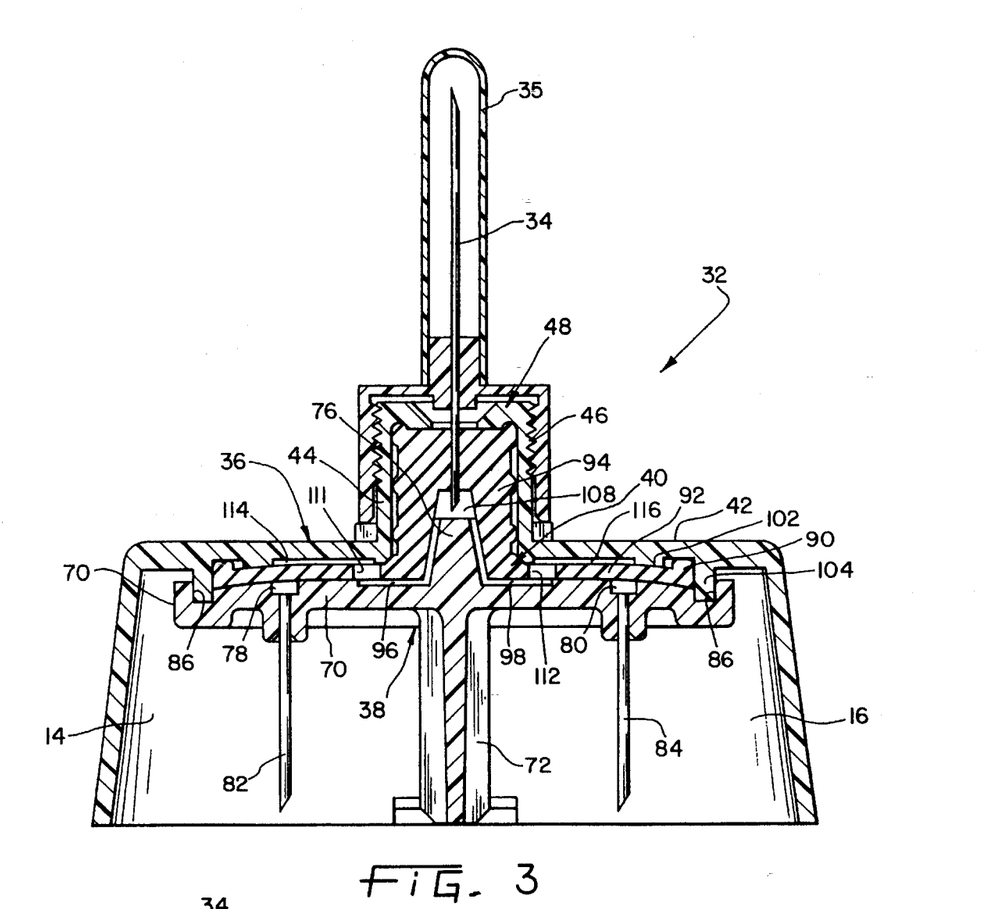
FIG. 3 is an enlarged view of the manifold assembly of FIG. 1.
Figure 4:
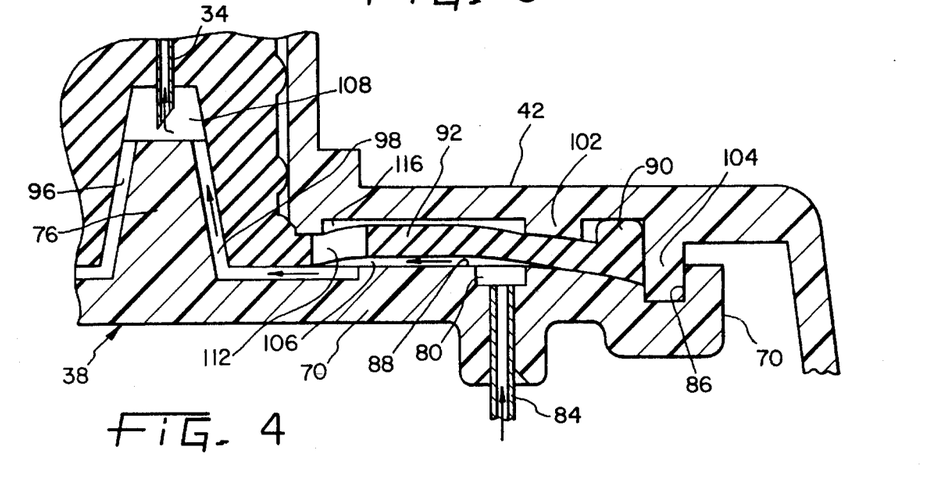
FIG. 4 is an enlarged view of a portion of the manifold assembly of FIG. 3, particularly showing the fluid flow path from one of the cartridges through the manifold assembly.

As shown in FIGS. 2 and 3, channels 96 and 98 are provided in rear housing 38. In particular, each channel 96, 98 comprises a recessed portion extending from septum openings 111, 112 along seal face 88 and along the length of raised section 76 onto the top portion 100 of raised section 76. The portions of seal face 88 between septum openings 111, 112 to inlet ports 78, 80 comprise the functional sealing face.

FIG. 3 illustrates all three components of manifold assembly 32 in its assembled condition. Specifically, septum 40 is placed within front housing 36 such that center portion 94 of septum 40 extends within the hollow needle attachment portion 44 of front housing 36. Beaded groove 90 of septum oval portion 70 is contained within a region defined between projections 102 and 104 on front housing 36. The rear housing 38 is then placed over septum 40 within front housing 36 in order to encapsulate septum 40 between the two parts. Specifically, projection 104 of front housing 106 extends into groove 86 of rear housing 38 and is ultrasonically welded thereto to form a hermetic seal therebetween.

As shown in FIG. 3, a check valve function is provided by body portion 92 of septum 40 being preloaded against seal face 88 to form a tight seal therebetween. This preload may be caused by bending the normally flat septum body portion 92 around the curved seal face 88. Alternatively, the preload may be caused by compression of body portion 92 between front 36 and rear 38 housings. In the disclosed embodiment, two check valves are disclosed, one in conjunction with cartridge 14 and another in conjunction with cartridge 16.

A fluid path from cannula 84 to delivery needle 34 is shown in FIG. 4. In particular, upon an injection force being applied by user, piston 20 (FIG. 1) is forced forwardly thereby pressurizing the fluid within cartridge 16. This increases the pressure at the inlet port 80 of rear housing 38 thereby forcing elastomeric body portion 92 of septum 40 upwardly into recessed area 116 as shown in FIG. 4. The amount of deformation of body portion 92 in FIG. 4 is exaggerated for illustration purposes. The deformation of body portion 92 creates a fluid path 106 which is in fluid communication with channel 98 formed in rear housing 38. Fluid then proceeds into mixing area 108 and out through delivery needle 34.

After injection has been completed, there will be a small amount of medication fluid in mixing area 108 and paths 96 and 98. It is desirable to ensure that this liquid cannot migrate back into cannulas 82, 84 and contaminate the fluid within cartridges 14 and 16. As shown in FIG. 3, septum 40 includes openings 111 and 112 therein. These openings are in fluid communication with flow paths 96 and 98, respectively. In addition, openings 111 and 112 are in communication with recessed areas 114 and 116 which are formed within front manifold housing 36.

Figure 5:
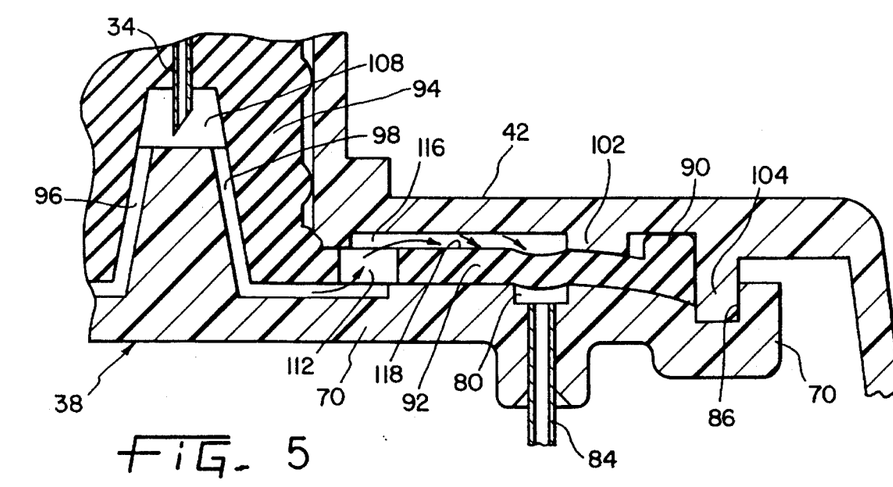
FIG. 5 is a view of the portion of the manifold assembly illustrated in FIG. 4, particularly showing the flow of fluid from an opposite cartridge causing fluid pressure to be exerted on the back surface of the check valve of the assembly.

Recessed area 116 constitutes a flow path as shown in FIG. 5. Thus, residual fluid within path 98 will migrate through opening 112 and into recessed area 116 in order to exert a fluid pressure on the back surface 118 of expandable body portion 92. This fluid pressure forces expandable body portion 92 into tighter engagement with seal face 88 of rear housing 38 to ensure that no fluid enters through the interface therebetween. Thus, when fluid pressure in recessed area 116 exceeds the pressure at the inlet port 80, the seal pressure of the check valve is increased, i.e., the valve is self-energizing. Likewise, residual fluid in path 96 would migrate through opening 111 and into recessed area 114 in order to provide a similar hydraulic closing force onto the check valve opposite that defined by expandable body portion 92.

The self-energizing check valves of the manifold assembly described herein are also desirable in instances in which the user desires to inject only medication from injector apparatus 10. For example, a user may desire to inject mixed doses of insulin in the morning and evening, but only fast acting insulin in the afternoon. In this instance, the check valve structure of manifold assembly 32 would ensure that fluid flowing, for example, from cartridge 14 through cannula 82, fluid path 114, septum opening 111, fluid path 96, mixing area 108, and out through needle 34 would not enter cannula 84 between seal face 88 and valve body 92. As shown in FIG. 5, the fluid entering through path 98 and through septum opening 112 would flow into closed ended path 116 thereby exerting a downward force onto back surface 118 of valve body portion 92 thereby ensuring that fluid would not enter into cannula 84 upon injection of only the fluid contained in cartridge 14.

In another aspect of the present invention, manifold assembly 32 may be removable from the distal end of an injection apparatus to enable the user to change the cartridges, once the cartridges have been emptied. Once removed, it is important that the manifold assembly be inserted back onto the injector apparatus in its original radial orientation with respect to the injector housing. For example, assuming cartridge 14 contains a fast acting insulin, and cartridge 16 contains an intermediate acting insulin, once cartridge 14 is replaced with a new cartridge containing fast acting insulin, it is important that cannula 82 be inserted back into cartridge 14. It would be undesirable for the manifold assembly to be oriented 180° with respect to its original orientation, in which instance cannula 82 would be inserted into cartridge 16, whereby the residual fluid within cannula 82 could contaminate the fluid within cartridge 16 with a different type of insulin. In order to ensure that manifold assembly 32 is properly rotatably oriented onto the distal end of an injection apparatus, a series of protrusions and grooves are provided in both manifold assembly 32 and the distal end of the injector apparatus.

Figure 7:
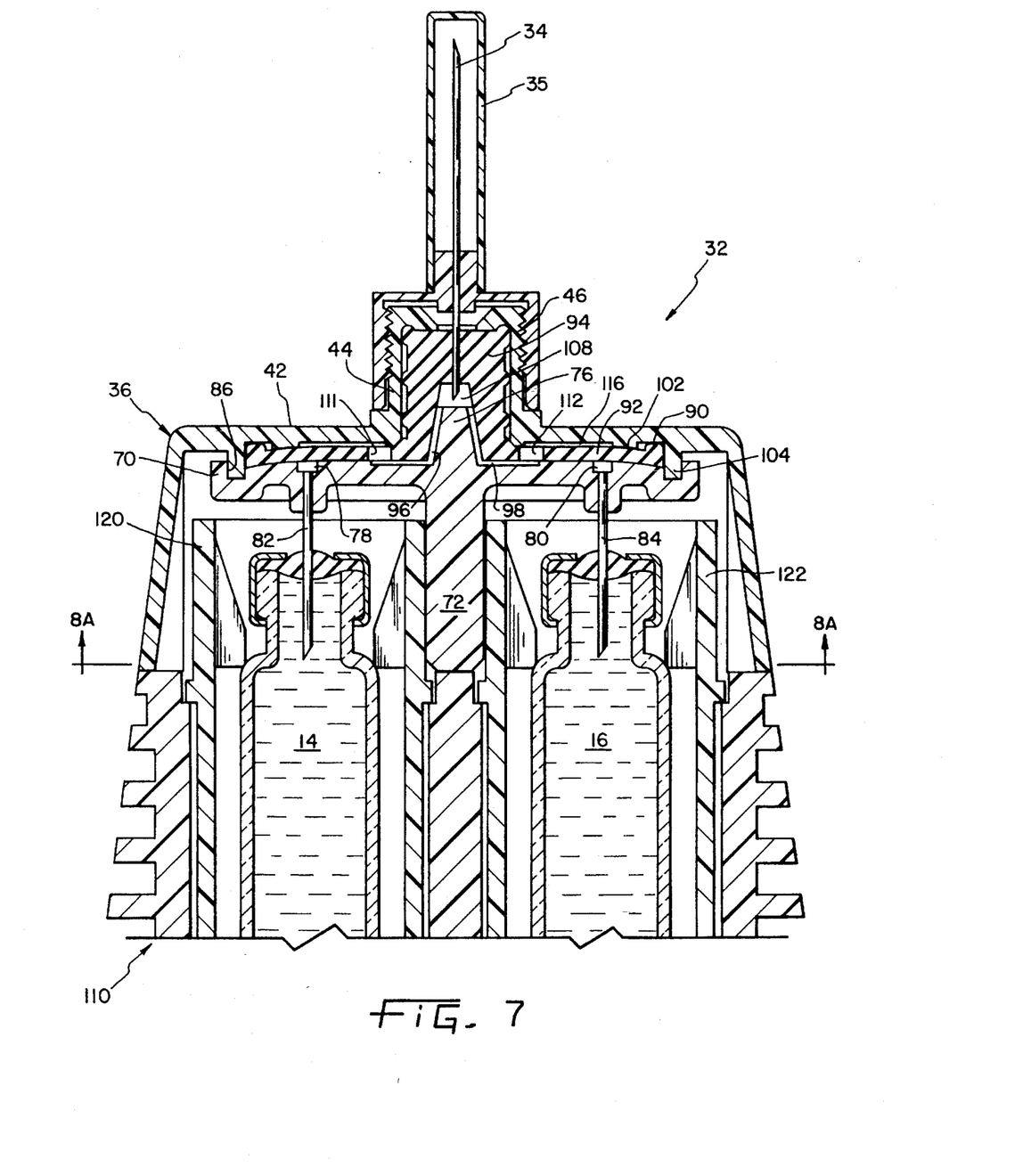
FIG. 7 is a cross sectional view of the distal end of a fully assembled injection apparatus, wherein a manifold assembly is secured to a second embodiment of an injection apparatus.
Figure 8A:
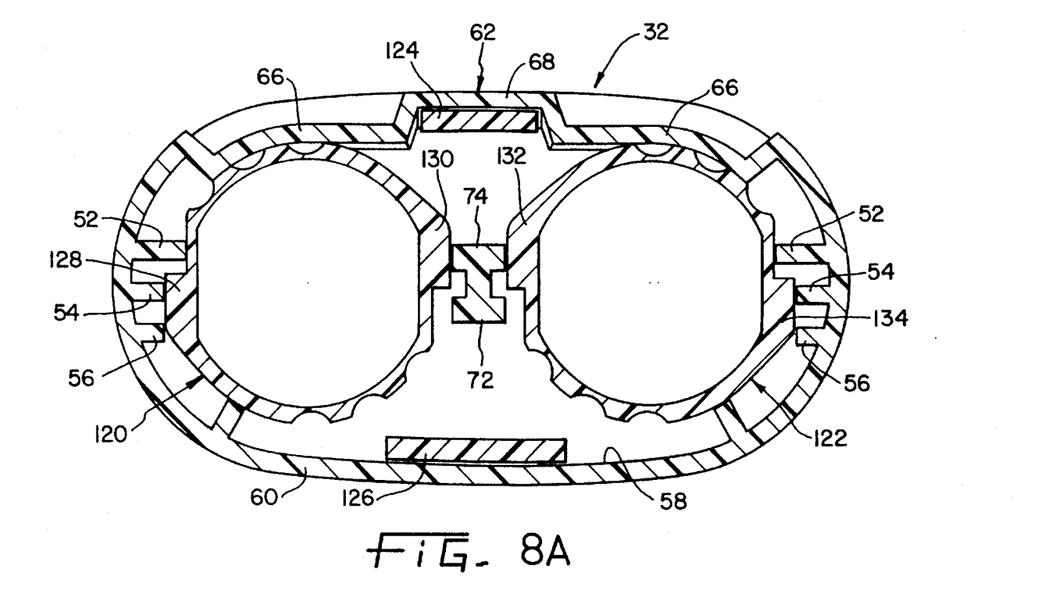
FIG. 8A is an enlarged sectional view of the apparatus of FIG. 7, taken along line 8A—8A in FIG. 7 and particularly showing the cartridge retainers in their respective locked positions and the manifold assembly in proper orientation and alignment with the distal end of the housing body.
Figure 8B:
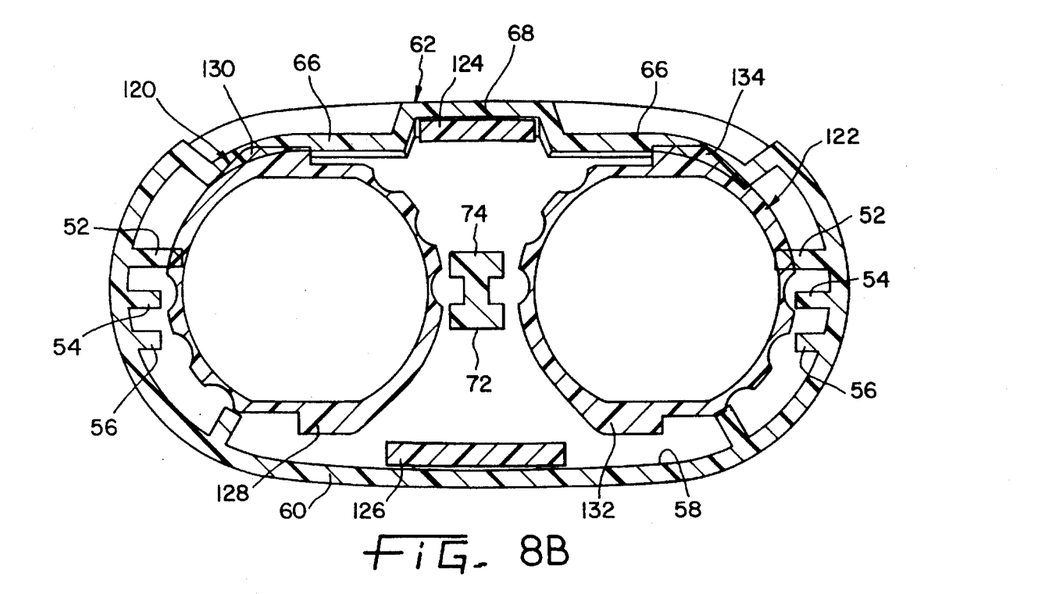
FIG. 8B is a view similar to FIG. 8A, except that the cartridge retainers are in their unlocked positions, resulting in an improper alignment between the manifold and the cartridge retainers.
Figure 8C:
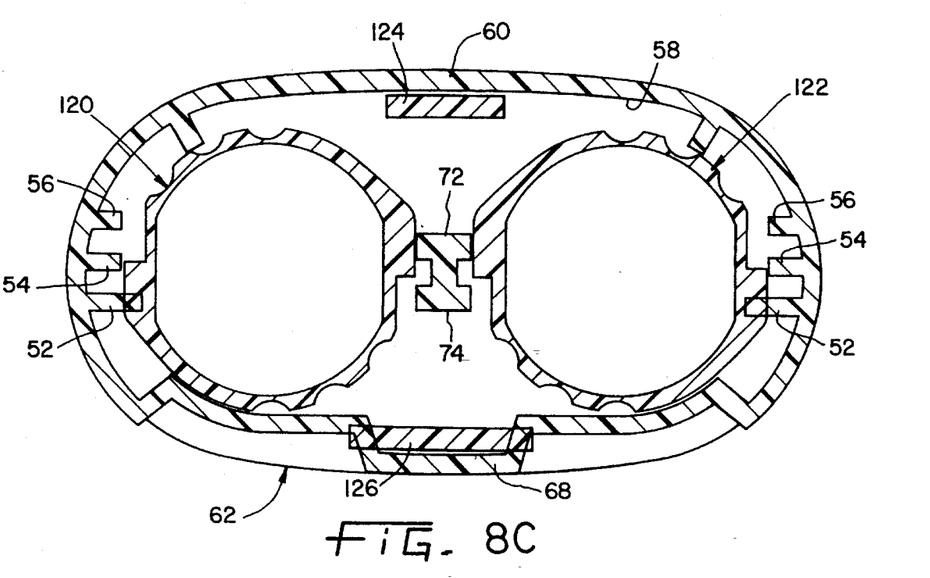
FIG. 8C is a view similar to FIG. 8A, except that the manifold has been rotated 180°, resulting in an improper alignment between the manifold and the distal end of the injector housing.

As shown in FIGS. 7 and 8A, manifold assembly 32 is shown to be oriented properly with respect to the distal end of an injector apparatus 110. Injector apparatus 110 is similar to injector apparatus 10, except that apparatus 110 includes cartridge retainers 120, 122 that include end portions which extend beyond the distal end of apparatus 110. In addition, apparatus 110 includes alignment projections 124 and 126 extending out from the distal end of the apparatus, as shown in FIGS. 8A, 8B, and 8C. Referring to FIG. 8A, projection 124 is sized to fit within recessed region 68 of the front housing 32. However, as shown in FIG. 8C, if a user rotates manifold assembly 180° with respect to the injector housing, the manifold cannot be snapped in place onto the distal end of apparatus 110 because recessed region 68 cannot be fitted over housing projection 126. The inability to snap manifold assembly 32 onto the distal end of apparatus 110 indicates to the user that the manifold assembly is incorrectly oriented with respect to the injector housing.

In apparatus 110, it is desirable that cartridge retainers 120, 122 be locked into position before the manifold assembly is snapped into place. In one embodiment, the proximal ends (not shown) of cartridge containers 120, 122 include bayonet couplings that are each inserted into a respective bayonet socket (not shown) formed in apparatus 110. The containers are not locked into position until each of the containers have been rotated 90° with respect to the injector housing, thereby causing the bayonet protrusions to become firmly engaged in the bayonet socket grooves.

It is desirable to provide a mechanism to ensure that the injector apparatus cannot be used unless the retainers have been locked. Referring to FIGS. 8A, 8B, and 8C, the distal end of cartridge 120 includes an outer peripheral surface having radial projections 128, 130. Similarly, the distal end of cartridge 122 includes an outer peripheral surface having radial projections 132, 134. FIG. 8B illustrates the radial positions of cartridges 120 and 122 upon inserting the cartridges into recesses in apparatus 110. If the manifold is attempted to be placed over these retainers in these initial radial positions, it is seen that an interferences occur between indented region 66 of the manifold and retainer projections 130 and 134. There is also an interference between manifold projections 52 and the outer periphery of retainers 120, 122. These interferences prevent the manifold from being placed over the retainers, thereby indicating to the user that the retainers have not been locked into position with respect to the apparatus.

Once retainers 120, 122 have each been rotated clockwise 90° with respect to the injector housing, as shown in FIG. 8A, manifold 32 can be placed over the retainers because the protrusions in manifold front housing 36 are in alignment with the recesses in the retainers.

It should be noted that a variety of individual geometric shapes and designs may be used in order to ensure that both the manifold assembly and the cartridge retainers are properly rotationally aligned with respect to the housing prior to insertion of the manifold into the distal end of the injector housing.

It will be appreciated that the foregoing is presented by way of illustration only, and not by way of any limitation, and that various alternatives and modifications may be made to the illustrated embodiment without departing from the spirit and scope of the invention.

What is claimed is:

1. A medication dispensing device for effecting the simultaneous delivery of two injectable products to a patient, comprising:

a housing;

a first container mounted to said housing and including a first plunger, a first exit end and a first injectable product between said first plunger and said first exit end;

a second container mounted to said housing and including a second plunger, a second exit end and a second injectable product between said second plunger and said second exit end;

first and second drive stems disposed in said housing and being drivingly coupled to said first and second plungers;

a drive assembly mounted to said housing and drivingly coupled to said first and second drive stems to axially advance said first and second drive stems upon actuation of said drive assembly, thereby axially advancing said first and second plungers to effect delivery of first and second dosages out of said first and second containers, respectively; and a manifold secured to said exit ends of said first and second cartridges and comprising a manifold housing including a first cannula extending into said first cartridge and a second cannula extending into said second cartridge, said manifold housing including a delivery needle therein for delivery therethrough of injectable product, wherein a first fluid path for the first injectable product is formed in said manifold housing from said first cannula to said delivery needle, and a second fluid path for the second injectable product is formed in said manifold housing from said second cannula to said delivery needle, said manifold further including a pressure-actuated valve in said second fluid path, said valve being sufficiently flexible to move in a first direction to open and thereby permit the flow therethrough of the second injectable product upon the expulsion of the second injectable product out of said second cannula, said manifold including a third fluid path between said first fluid path and said valve, said third fluid path configured to divert a portion of the fluid flowing in said first fluid path to said third fluid path and onto said valve to create a fluid force on said valve in a second and opposite direction from said first direction.

2. A medication dispensing device for effecting the simultaneous delivery of two injectable products to a patient, comprising:

a housing;

a first container mounted to said housing and including a first plunger, a first exit end and a first injectable product between said first plunger and said first exit end;

a second container mounted to said housing and including a second plunger, a second exit end and a second injectable product between said second plunger and said second exit end;

first and second drive stems disposed in said housing and being drivingly coupled to said first and second plungers;

a drive assembly mounted to said housing and drivingly coupled to said first and second drive stems to axially advance said first and second drive stems upon actuation of said drive assembly, thereby axially advancing said first and second plungers to effect delivery of first and second dosages out of said first and second containers, respectively; and a manifold secured to said exit ends of said first and second cartridges and comprising a manifold housing including a first cannula extending into said first cartridge and a second cannula extending into said second cartridge, said manifold housing including a delivery needle therein for delivery therethrough of injectable product, wherein a first fluid path for the first injectable product is formed in said manifold housing from said first cannula to said delivery needle, and a second fluid path for the second injectable product is formed in said manifold housing from said second cannula to said delivery needle, said manifold further including valve means in said second fluid path for regulating the flow of fluid in said second fluid path, said valve means opening in a first direction to permit the flow of the second injectable product therethrough upon the expulsion of the second injectable product out of said second cannula, said manifold including a third fluid path means between said first fluid path and said valve means, said third fluid path means configured to divert a portion of the fluid flowing in said first fluid path to said third fluid path means and onto said valve means to create a fluid force on said valve means in a second and opposite direction from said first direction.

3. A manifold assembly for attachment to an outlet end of a medication dispensing device for enabling the delivery of two injectable products through a single delivery needle, the manifold comprising:

a first housing including a delivery needle therein for delivery of the injectable products therethrough a second housing including first and second cannulas extending therethrough; and a rubber septum disposed between said first and second housings, wherein a first fluid path for the first injectable product is formed in said manifold from said first cannula to said delivery needle, and a second fluid path for the second injectable product is formed in said manifold housing from said second cannula to said delivery needle, wherein a portion of a first surface of said septum is in fluid-tight engagement with a sealing surface of said second housing to define a pressure-actuable check valve in said second fluid path, said check valve being sufficiently flexible such that upon a given increase in fluid pressure in said second cannula, said first surface of said septum is moved away from said sealing surface of said second housing, thereby permitting the flow of the second injectable product through said check valve upon expulsion of the second injectable product out of said second cannula, said first housing including a third fluid path extending from said second fluid path to a second surface of said septum, said second surface being opposite from said first surface, said third fluid path enabling a portion of the fluid in said second fluid path to migrate to said third fluid path to create a hydraulic force on said second surface of said septum.

4. A medication dispensing device for effecting the simultaneous delivery of two injectable products to a patient, comprising:

a housing having a proximal end and a distal end, said distal end including a first mating surface extending therefrom;

a first container disposed in said housing and including a first plunger, a first exit end and a first injectable product between said first plunger and said first exit end;

a second container disposed in said housing and including a second plunger, a second exit end and a second injectable product between said second plunger and said second exit end;

first and second drive stems disposed in said housing and being drivingly coupled to said first and second plungers;

a drive assembly mounted to said housing and drivingly coupled to said first and second drive stems to axially advance said first and second drive stems upon actuation of said drive assembly, thereby axially advancing said first and second plungers to effect delivery of first and second dosages out of said first and second containers, respectively; and a manifold securable to said distal end of said housing, said manifold including a second mating surface extending therefrom, wherein said manifold is securable to said distal end of said housing when said manifold is oriented in a first radial position with respect to said housing such that said first mating surface matingly engages said second mating surface, said manifold being configured such that it cannot be secured to said housing when said manifold is oriented in a radial position other than said first radial position, thereby causing said second mating surface to not matingly engage said first mating surface.

5. A medication dispensing device for effecting the simultaneous delivery of two injectable products to a patient, comprising:

a housing having a proximal end and a distal end;

a first cartridge disposed in a first retainer and including a first plunger, a first exit end and a first injectable product between said first plunger and said first exit end, said first retainer being disposed within said housing, wherein a first end portion of said first retainer extends beyond said distal end of said housing, said first retainer being rotatable with respect to said housing between a first locked position and a first unlocked position;

a second cartridge disposed in a second retainer and including a second plunger, a second exit end and a second injectable product between said second plunger and said second exit end, said second retainer being disposed within said housing, wherein a second end portion of said second retainer extends beyond said distal end of said housing, said second retainer being rotatable with respect to said housing between a second locked position and a second unlocked position;

first and second drive stems disposed in said housing and being drivingly coupled to said first and second plungers;

a drive assembly mounted to said housing and drivingly coupled to said first and second drive stems to axially advance said first and second drive stems upon actuation of said drive assembly, thereby axially advancing said first and second plungers to effect delivery of first and second dosages out of said first and second containers, respectively; and a removable manifold for mixing the first and second dosages and enabling a mixed dosage to be delivered therethrough, said manifold being movable over said first and second end portions and securable to said distal end of said housing while said first and second retainers are in their first and second locked positions, respectively, and wherein said manifold is incapable of being movable over said first and second end portions while at least one of said first and second end portions is in its respective said unlocked position.

* * * * *